US00PP24406P2

(12) United States Plant Patent
Kordes

(10) Patent No.: US PP24,406 P2
(45) Date of Patent: Apr. 29, 2014

(54) FLORIBUNDA ROSE PLANT NAMED 'KORAMFLUSA'

(50) Latin Name: *Rosa hybrida*
Varietal Denomination: KORamflusa

(75) Inventor: Tim-Hermann Kordes, Klein Offenseth-Sparrieshoop (DE)

(73) Assignee: W. Kordes' Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 76 days.

(21) Appl. No.: 13/573,127

(22) Filed: Aug. 24, 2012

(51) Int. Cl.
*A01H 5/00* (2006.01)

(52) U.S. Cl.
USPC ..... Plt./143

(58) Field of Classification Search
USPC ..... Plt./143, 141
See application file for complete search history.

*Primary Examiner* — Kent L Bell

(57) ABSTRACT

A new and distinct variety of rose with long lasting, novel yellow flowers with pink edges, and attractive foliage with excellent disease resistance. It exhibits vigorous upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORamflusa'. The new variety of rose plant of the present invention originated from a controlled crossing in a breeding program of two distinct parents during the summer of 2002. The crossing was between an 'un-named seedling', the seed parent, and another 'un-named seedling', the pollen parent from the same inventor.

CROSS REFERENCES AND FEDERAL R&D STATEMENT

There are no cross referenced or related applications. This variety was developed without the aid of any research grant.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORamflusa'.

SUMMARY OF THE INVENTION

The new rose plant may be distinguished from its seed parent, an 'un-named seedling', by the following combination of characteristics:

1. 'KORamflusa' has medium sized yellow flowers with pink edges, whereas the 'un-named seedling' has large sized apricot flowers.
2. 'KORamflusa' has better disease resistance than the 'un-named seedling'.

The new rose plant may be distinguished from its pollen parent, an 'un-named seedling', by the following combination of characteristics:

1. The flowers of 'KORamflusa' are yellow with pink edges and have a double petal count, whereas the flowers of the 'un-named seedling' are cream yellow and have a semi-double petal count.

2. 'KORamflusa' has an upright to bushy growth habit, whereas the 'un-named seedling' has a bushy growth habit.

The objective of the hybridization was to create a new and distinct rose plant with unique qualities, such as:

1. Uniform growth and flowering;
2. Abundant attractive, recurrent yellow flowers with pink edges;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORamflusa' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORamflusa' was selected in May, 2003 from the seedling beds to be asexually propagated for further evaluation. The first asexual propagation of 'KORamflusa' was done by budding to seedling understocks in July, 2003 at the inventor's nursery in Offenseth-Sparrieshoop, Germany.

This initial and other subsequent propagations conducted in controlled environments demonstrate that 'KORamflusa' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORamflusa'.

DETAILED BOTANICAL DESCRIPTION

The following is a description of 'KORamflusa', as observed growing in July, 2012 in a nursery in Jackson County, Oreg. on plants 1 year of age. Color references are made using The Royal Horticultural Society (London, England) Colour Chart, 2001 except where common terms of color are used.

For a comparison, several physical characteristics of the rose variety 'KORgohowa', a rose variety from the same inventor described and illustrated in U.S. Plant Pat. No. 22,539 and issued on Mar. 6, 2012 are compared to 'KORamflusa' in Chart 1.

CHART 1

| Characteristic | 'KORamflusa' | 'KORgohowa' |
|---|---|---|
| Petal Count | 45-55 | 50-60 |
| Number of Pistils | 90-110 | 35-45 |
| Petal Edge | Entire to erose | Entire |

Parents:

*Seed parent.*—An 'un-named seedling'.

*Pollen parent.*—An 'un-named seedling'.

Classification:

*Botanical classification.*—*Rosa hybrida* 'KORamflusa'.

*Commercial classification.*—Floribunda rose.

FLOWER AND FLOWER BUD

Blooming habit: Recurrent.

Flower bud:

*Size.*—Upon opening, 28 mm in length from base of receptacle to distal end of bud and 25-30 mm diameter at its widest point.

*Bud form.*—Short. Globular.

*Bud color.*—As sepals first unfold, bud color is Yellow-Orange Group 15B, with intonations of Red Groups 45C to 46A in sun-exposed areas. When ¼ open, the upper surface of petals is Yellow Group 12A with overtones of Yellow-Orange Group 23B in the middle zone, and Red Group 36A in the marginal zone. Intonations of Red Group 43D appear on sun-exposed edges. The lower surface is Yellow Group 13B, with Yellow-Orange Group 19C in the marginal zone and intonations of Red Group 44D and 45D on those areas of the petals that have been exposed to direct sunlight. Outermost petals have intonations of Yellow-Green Group 144C and of Red Group 53A to 53B.

*Sepals.*—Color: Upper surface: Yellow-Green Group 144A and 144C. Lower surface: Yellow-Green Group 144D and N144D. Intonations of Greyed-Purple Group 182A and 183A on upper and lower surfaces. Size: Average 20-30 mm (l)×8 mm (w). Shape: Weak to moderate foliaceous appendages on 3-4 of the 5-6 sepals. Apex: Apiculate. Base: Flat at union with receptacle. Quantity: Most flowers have 5, some have 6. Surface texture: Upper side: Smooth. Lower surface: Pubescent. Margins: Slightly pubescent with numerous stipitate glands.

Receptacle:

*Surface.*—Smooth.

*Color.*—Green Group 143C, with intonations of Greyed-Purple Groups 185A and 185B.

*Shape.*—Urn-shaped.

*Size.*—6 mm (h)×8 mm (w).

Pedicel:

*Surface.*—Smooth.

*Length.*—30 to 45 mm average length.

*Diameter.*—3 to 4 mm average diameter.

*Color.*—Greyed-Purple Group 184A and 185A.

*Strength.*—Strong.

Peduncle:

*Surface.*—Smooth.

*Length.*—35 to 75 mm average length.

*Diameter.*—3 to 4 mm average diameter.

*Color.*—Yellow-Green Group 144B and 144C, with intonations of Greyed-Orange Group 174A.

*Strength.*—Strong.

*Borne.*—Multiple flower buds per stem, most commonly 6 to 10, with some single flowers and small clusters of 3 to 4.

Flower bloom:

*Fragrance.*—Light.

*Duration.*—On the plant 5 to 6 days. Long lasting. As a cut flower, 3 to 4 days. Senesced petals drop away cleanly.

*Size.*—Small for a floribunda rose. When open, the average flower diameter is 60 mm and the average flower height is 33 mm.

*Form.*—Shape of flower when viewed from the side: Upon opening, upper part: Flattened convex. Upon opening, lower part: Concave. Open flower, upper part: Flattened convex. Open flower, lower part: Concave.

Color:

*Upon opening, petals.*—Outermost petals: Outer Side: Yellow Group 12B and 10B, with intonations of Orange-Red Group 33C, Red Group 48A and 53B, and Red-Purple Group 71A. Inner Side: Yellow Group 7A to 9A, with margins of Orange-White Group 159A and intonations of Orange-Red Group 35A and Red Group 53C and 53D.

*Innermost petals.*—Outer Side: Yellow Group 8B and 13B, with Yellow Group 8A in the basal zone. Inner Side: Yellow Group 10A, with Yellow Group 9A and 12A in the basal zone and intonations of Yellow-Orange Group 16A.

*After opening, petals.*—Outermost petals: Outer Side: Yellow Group 7A, with Yellow-Orange Group 20D in the marginal zone and intonations of Orange-Red Group 31C, Red Group 46A, and Red-Purple Group 64A. Inner Side: Yellow Group 7A, with Yellow-Orange group 23D in the marginal zone and intonations of Red Group 50A to 54A. Innermost petals: Outer Side: Yellow Group 9C. Inner Side: Yellow Group 11B to 11C.

*After opening, basal petal spots.*—Basal petal spot, outermost petals: Inner Side: Yellow Group 12A. Basal petal spot, innermost petals: Outer Side: Yellow Group 9A. Inner Side Yellow Group 12A.

General tonality: On open flower, Yellow Group 13C and Yellow-Orange Group 16A. No change in the general tonality at the end of the fourth day. Afterwards, general tonality is Yellow Group 8B and 8C, with intonations of Red Group 46C and 53C.

Petals:

*Petal count.*—Very Double.

*Average range.*—Approximately 45 to 55 petals under normal conditions.

*Petal reflex.*—Outer petals reflex strongly.

*Petal edge.*—Inner petals are entire to undulating. Outermost petals are erose.

*Petal shape.*—Obovate. Apex shape is obtuse. Shape of base is cuneate.

*Petal size.*—25-30 mm (l)×20-25 mm (w).

*Thickness.*—Average.

*Petal arrangement.*—Not formal.

Petaloids:

*Petaloid count.*—Average of 4-7 per flower.

*Petaloid size.*—12-20 mm (l)×7-12 mm (w).

*Petaloid color.*—Color of inner side is Yellow Group 10A with overtones of Yellow Group 16A, fading to Yellow Group 10C with intonations of Red Group 39C. Color of outer side is Yellow Group 10A, fading to Yellow Group 5C with intonations of Red Group 39A and 53C.

*Petaloid texture.*—Thick.

*Margins.*—Some smooth, some indented.

*Petaloid shape.*—Most commonly spatulate, with some petaloids highly irregular. Many petaloids hang from long, attenuate bases resembling filaments 3-5 mm in length. Apex: Obtuse. Base: Attenuate.

Reproductive organs:

*Pistils.*—Approximately 90-110 present. Stigmas: Location:. Some slightly inferior in position to anthers, some slightly superior. Color: Yellow Group 3A. Styles: Length: About 6-8 mm long. Color: Yellow-Group 2D.

*Stamens.*—Approximately 100-120 on average and regularly arranged. Anthers: Size: Average 1.5 mm (l)×1 mm (w). Pollen: Generally present. Color: Greyed-Orange Group 163A. Filaments: Color: Yellow Group 9A. Length: 7 mm.

THE PLANT

*Growth.*—Vigorous growth.

*Plant habit.*—Upright to bushy habit. When grown as an own root plant, the average plant height is 70 cm and the average plant width is 40 cm.

*Blooming.*—Floriferous.

*Stems.*—Stem color: Young wood: Yellow-Green Group 144B, with intonations of Greyed-Orange Group 176A. Older wood: Yellow-Green Group 144A. Stem surface: Young wood: Smooth. Older wood: Smooth.

*Prickles.*—Present. Incidence: Average of 11 per each 10 cm of stem. Limited numbers of small, fine prickles of less than 2 mm in length also present. Size: Average length: 8 mm. Color: Immature prickles: Yellow Group 5C. Mature prickles: Grey-Brown Group N 199D. Shape: Linear to slightly concave. Anthocyanin: Intonations of Orange-Red Group 34C found on immature prickles.

*Leaves and leaflets.*—Normally 7 leaflets on normal leaves in middle of the stem. Venation pattern: Pyramidal net pattern. Leaf size: 120 mm (l)×70 mm (w). Abundance: Average. Texture: Leathery, thick. Upper side of leaflet: Semi-glossy, smooth. Under side of leaflet: Matte, smooth. Color, mature foliage: Upper Leaf Surface: Yellow-Green Group 147A. Lower Leaf Surface: Yellow-Green Group 147B to 147C. Color, juvenile foliage: Upper Leaf Surface: Yellow-Green Group 144A. Lower Leaf Surface: Yellow-Green Group 144A. Anthocyanin intonation: Intonations of Greyed-Purple Group 183A present on leaf margins.

*Stipules.*—Size: 15-25 mm long, 6-8 mm from distal tip to distal tip. Stipule color: Yellow-Green Group 144A. Margins: With abundant stipitate glands. Shape: Apex: Apiculate. Base: Flat.

*Petiole.*—Length: Average 22 mm. Diameter: Average 2 mm. Petiole color: Yellow-Green Group 145C. Underneath: Yellow-Green Group 146C. Margins: Limited numbers of stipitate glands. Anthocyanin: Slight intonations of Greyed-Red Group 182A on the upper side. Prickles: Small prickles occasionally occur on underside.

*Petiole rachis.*—Length: Average 15-20 mm. Diameter: Average 1.5 mm. Color: Yellow-Green Group 144A to 144C. Intonations of Greyed-Purple Group 183A present on upper side. Prickles: A few small prickles underneath. Stipitate glands: Limited numbers of stipitate glands on margins.

*Leaflets.*—Size: Average size of the terminal leaflet is 45 mm (l)×33 mm (w). Shape: Ovate. Base: Obtuse. Apex: Acute. Margins: Serrated. Surface: Upper surface: Semi-glossy. Lower surface: Matte. Texture: Thick, leathery. Arrangement: Odd pinnate. Venation Reticulate.

Hips/seed formation: None observed.

Winter hardiness: To date, the variety has been grown successfully in Zones 5-9.

Disease resistance: Excellent resistance to Powdery mildew (*Sphaerotheca pannosa*), blackspot (*Diplocarpon rosae*), rust (*Phragmidium* sp.), and *Botrytis* (*Botrytis cinerea*) diseases under normal growing conditions in Jackson County, Oreg.

I claim:

1. A new and distinct variety of rose plant, as described and illustrated herein.

* * * * *

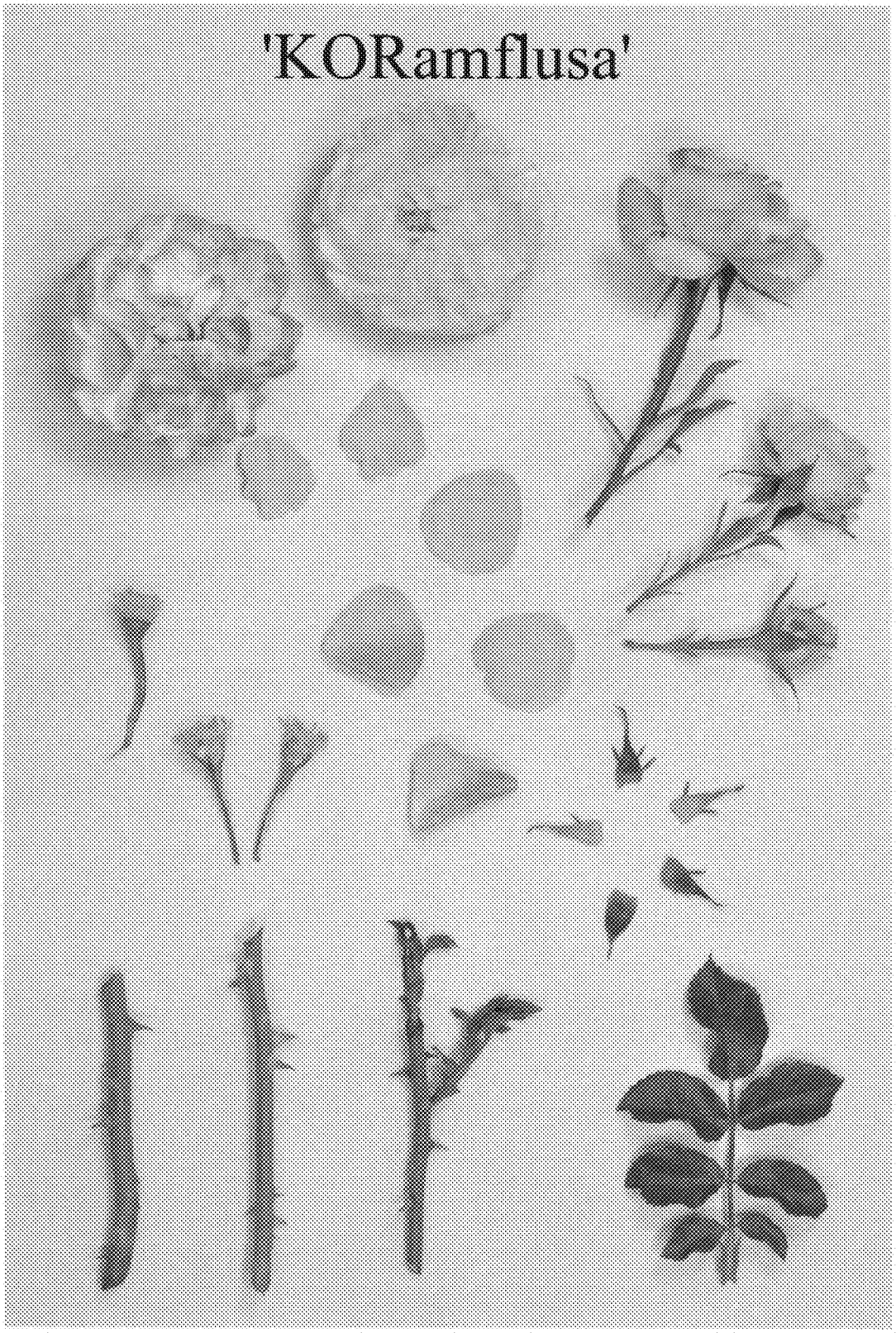
'KORamflusa'